United States Patent [19]

Wallace

[11] Patent Number: 4,873,986
[45] Date of Patent: Oct. 17, 1989

[54] DISPOSABLE APPARATUS FOR MONITORING INTRAUTERINE PRESSURE AND FETAL HEART RATE

[75] Inventor: William D. Wallace, Salt Lake City, Utah

[73] Assignee: Utah Medical Products, Salt Lake City, Utah

[21] Appl. No.: 186,894

[22] Filed: Apr. 27, 1988

Related U.S. Application Data

[63] Continuation-in-part of Ser. No. 033,420, Apr. 1, 1987, Pat. No. 4,785,822.

[51] Int. Cl.⁴ .................................................. A61B 5/02
[52] U.S. Cl. .................................... 128/670; 128/675; 128/698; 128/700; 128/775
[58] Field of Search ............... 128/642, 670, 672, 673, 128/675, 698, 699, 700, 748, 775, 784–786; 604/172, 265; 73/4 R, 708, 715, 721, 740

[56] References Cited

U.S. PATENT DOCUMENTS

| | | | |
|---|---|---|---|
| 3,038,465 | 6/1962 | Allard et al. | 128/675 |
| 3,710,781 | 1/1973 | Hutchins et al. | 128/675 |
| 3,946,724 | 3/1976 | LaBlanc | 128/675 |
| 4,136,681 | 1/1979 | Hon | 128/2 R |
| 4,191,193 | 3/1980 | Seo | 128/675 |
| 4,252,131 | 2/1981 | Hon et al. | 128/748 |
| 4,274,423 | 6/1981 | Mizuno et al. | 128/675 |
| 4,325,387 | 4/1982 | Helfer | 128/748 |
| 4,407,296 | 10/1983 | Anderson | 128/675 |
| 4,509,370 | 4/1985 | Hirschfeld | 73/705 |
| 4,517,984 | 5/1985 | Perlin | 128/670 |
| 4,576,181 | 3/1986 | Wallace et al. | 128/675 |
| 4,588,398 | 5/1986 | Daugherty et al. | 604/265 |
| 4,601,706 | 7/1986 | Aillon | 128/673 |
| 4,611,600 | 9/1986 | Cohen | 128/675 |
| 4,754,753 | 7/1988 | King | 128/699 |

OTHER PUBLICATIONS

"Oesophageal Probe for Heart and Temperature Monitoring During Anaesthesia", Linnarsson et al., Med. & Bill. Eng., 1982.
"Intracardiac Catheter Tip Piezoresistive Pressure Gauge", The Review of Scientific Instruments, 31.9, pp. 987–991 (1960).
"An IC Piezoresistive Pressure Sensor for Biomedical Instrumentation", EE Transactions on Biomedical Engineering, BME-20:2, pp. 101-109 (1973).
"A Stable UltraMiniature Catheter-Tip Pressure Transducer", (1973).
"The Effect of Oxytocin Infusion on Uterine Activity Levels in Slow Labor", British Journal of Obstetrics and Gynaecology, (1985).

Primary Examiner—Max Hindenburg
Attorney, Agent, or Firm—Workman; Nydegger; Jensen

[57] ABSTRACT

A disposable apparatus for monitoring intrauterine pressure and fetal heart rate during labor and childbirth. The apparatus includes a semiconductor pressure transducer mounted on a substrate. In one embodiment, the substrate is secured within a flexible boot adapted to allow the pressure pulses present in a uterus to be communicated to the pressure transducer by way of a gel placed in aligned holes provided in both the substrate and the flexible boot. The pressure transducer is located at the leading end of a cable which includes electrical conductors. A plurality of electrodes are also disposed along the outer surface of the cable so as to be able to receive the electrical signals generated by the heart of the fetus. Each of the electrodes and the pressure transducer are connected to a monitor/display device by way of the conductors within the cable. The cable may be provided with an internal stiffening stylet to facilitate insertion of the apparatus into the uterus or other body compartment. The internal structure of the cable is provided with a vent channel which communicates with the semiconductor transducer and extends along the cable to a hole in the plug on the distal end of the cable, to permit calibration and/or referencing of the transducer to atmospheric pressure. In one embodiment a lumen is provided in the cable to allow sampling of body fluids or infusion of fluids into the body.

44 Claims, 4 Drawing Sheets

DISPOSABLE APPARATUS FOR MONITORING INTRAUTERINE PRESSURE AND FETAL HEART RATE

RELATED APPLICATIONS

This application is a continuation-in-part of U.S. patent application Ser. No. 033,420, filed Apr. 1, 1987, now U.S. Pat. No. 4,785,822, Nov. 22, 1988.

BACKGROUND

1. The Field of the Invention

This invention relates to apparatus used to monitor fetal condition during labor and childbirth. More particularly, the present invention is directed to a novel, disposable apparatus for use in direct measurement and monitoring of intrauterine pressure and fetal heart rate during labor and childbirth.

2. The Prior Art

Each year, approximately 3.5 million children are born within the United States. In order to assist physicians in treating a mother and child approaching childbirth, monitoring devices are quite commonly used during the final states of labor to monitor both the mother's uterine contractions and the fetal heart rate. Such monitoring devices can quickly provide the physician with information about the rate, duration, and intensity of the mother's uterine contractions and the effect of the contractions on the fetal heart rate. This information can help the physician ensure that oxygen and nutrients are being properly transferred from the mother to the fetus during labor and childbirth and can help the physician identify potential problems before they become life-threatening.

It is often the case that uterine contractions and fetal heart rate are monitored using devices which can be secured externally to the surface of the mother's abdomen. For example, a pressure sensitive button called a tocotransducer is often secured to the mother's abdomen to provide information about the frequency and duration of the uterine contractions. The fetal heart rate may be externally monitored by an ultrasound transducer, a phonotransducer, or some other suitable device.

In many cases, externally secured monitoring devices can provide sufficient information to enable a physician to treat the mother and child during labor and childbirth. It will be appreciated, however, that the use of external monitoring devices may give rise to large measurement errors in some cases due to extraneous noise and/or movement by the mother. In many labor and birthing situations, and particularly where there is a significant risk of complications, a physician may wish to have more accurate measurements than can be obtained using external monitoring devices.

In order to obtain more reliable and accurate information about the mother's uterine contractions, a physician will often initiate intrauterine pressure monitoring. In addition to providing information about the rate and duration of the uterine contractions, intrauterine pressure monitoring can also provide information about the intensity of the uterine contractions. Importantly, since the uterine pressure is being measured directly, errors in measurement due to extraneous noise and movement by the mother are less likely than with external monitoring devices.

One of the most widely used techniques for intrauterine pressure measurement and monitoring uses a fluid-filled catheter inserted into the uterus and then connected externally to a pressure transducer. In using this technique, a rigid guide tube is inserted just inside the mother's cervix. A special catheter is then threaded through the guide tube until it extends into the uterus approximately 15 to 20 centimeters (cm). This catheter is filled with some type of solution, such as, for example, a sterile saline solution. Once the catheter is in place, the guide tube is removed from the cervix and slid away from the mother along the catheter.

After the in-dwelling catheter is positioned as described above, the other end of the catheter is fluid coupled to a pressure transducer. The pressure transducer is then connected to some type of monitor device near the patient's bedside. Typical monitor devices include cathode ray tube display devices, digital display and/or recording devices, printers, and plotters.

In addition to the proper set-up of the measurement equipment in the above-described manner, it is also important to prime the catheter with a sterile solution so that any air bubbles within the catheter are removed and a continuous fluid column is provided from the pressure transducer to the tip of the catheter within the uterus. Then, when the mother's uterus thereafter contracts, the increased intrauterine pressure displaces the fluid within the catheter, and the pressure transducer detects a change in the intrauterine pressure. The pressure transducer generates electrical signals representing the intrauterine pressure, and such signals are then amplified and displayed by the monitor device. Usually, the monitor device is used to display the mother's intrauterine pressure as a function of time, along with the fetal heart rate, and this data can then be used by the physician and other medical personnel to appropriately diagnose and treat the mother and child.

As indicated previously, fetal heart rate may be externally monitored using an ultrasonic transducer, phonotransducer, or electrodes placed on the mother's abdomen. Alternatively, if desired by the physician, an electrode may be implanted into the fetus' skin (usually the scalp using a guide tube) with another electrode applied to the mother at a point near the uterus (usually the leg). Using an internal method for monitoring both intrauterine pressure and fetal heart rate provides more accurate measurements of these physiological parameters than any known external monitoring technique. For example, external fetal heart rate monitoring techniques may be ineffective if the fetus continually changes position.

While the foregoing techniques for monitoring intrauterine pressure and fetal heart rate are widely used and under proper circumstances can produce reliable measurements, there are a number of significant difficulties associated with these techniques. First, the necessity of using a rigid catheter guide tube to insert the pressure monitoring catheter and the fetal electrode into the uterus can make insertion of these components somewhat awkward and difficult, as well as posing a potential threat of puncturing the wall of the uterus and causing hemorrhage, or causing injury to the child. Moreover, since the distal end of the pressure monitoring catheter is typically secured to a needle or some other coupling device, it is difficult to remove the rigid guide tube from the catheter after the catheter is inserted. Often, the rigid guide tube makes it awkward to move the in-dwelling catheter around once it is inside the uterus of the patient, and the catheter may occasionally break, bend or become removed as a result of being pinched by the guide tube.

Another disadvantage of the above-described technique is that the fluid column in the pressure monitoring catheter necessarily opens into the uterus. As a result of fluid displacement in the catheter, amniotic fluid from the uterus invariably enters the catheter and may interfere with accurate pressure monitoring. Sometimes, an air bubble will also enter the catheter, or uterine tissue may obstruct the open end of the catheter. In such cases, it is necessary to flush the catheter with sterile solution to remove the air bubble or obstruction, and it may occasionally be necessary to replace the catheter altogether.

Another difficulty that arises with the use of an internal fetal heart rate electrode which is attached to the fetus' skin is that it cannot be used if the face of the fetus is presented first in the uterus. also, since the skin of the fetus is punctured by the electrode, infection may result or fetus body fluids (such as cerebral spinal fluid when scalp insertion is used) may leak into the uterus.

A further difficulty with the foregoing internal pressure monitoring technique is due to the difficulty of zero balancing the pressure transducer to ensure that the static readings it produces are accurate. A transducer is balanced in order to establish atmospheric pressure at the baseline or zero point from which the patient's intrauterine pressure is referenced.

A pressure transducer is often used with a disposable dome that fits over the transducer diaphragm. The dome has two ports, one on the side and one vertical. The side port is connected to the in-dwelling fluid-filled catheter after it is primed with sterile solution. The other port is generally used for balancing and calibration.

In order to balance the pressure transducer, the vertical port of the dome is opened to atmosphere and the other port is opened to the catheter inserted into the patient. The pressure transducer is then raised or lowered until the top of the vertical port is level with the position of the in-dwelling tip of the fluid-filled catheter. For each inch off the proper level, there will be an error in the pressure reading of about 2 millimeters (mm) of mercury (Hg). The monitor is then zeroed and the transducer port recapped.

The difficulty in accurately balancing the pressure transducer using the above-described technique for intrauterine pressure monitoring will be readily appreciated, since the tip of a catheter inside the mother's uterus cannot be seen. Consequently, the location of the tip of the catheter can only be estimated, and it is virtually impossible to determine whether the transducer is producing totally accurate pressure readings. One further disadvantage of the above-described internal pressure monitoring system is that there are potential errors in the transducer readings that may be introduced as a result of overly compliant tubing, or failure to adequately flush all air from the system prior to use. This will result in overdamping of the pressure readings.

One further problem is that in order for a transducer to function properly, the diaphragm of the transducer must be vented on one side to a substantially constant pressure. Typically, one side of the diaphragm of the transducer is vented to atmospheric pressure. However, in intracompartmental applications such as intrauterine monitoring, when a transducer is positioned within the uterus or other body compartment, it can be extremely difficult to properly vent the transducer, and the lack of proper venting can make it very difficult to obtain accurate pressure measurements.

BRIEF SUMMARY AND OBJECTS OF THE INVENTION

In view of the foregoing problems experienced with prior art techniques for monitoring intrauterine pressure and fetal heart rate, it is a primary object of the present invention to provide a disposable monitoring apparatus which combines the functions of pressure monitoring and heart rate monitoring, and which is safer, more accurate, and economical than prior art systems or apparatus.

It is another object of the present invention to provide an intrauterine fetal heart rate and pressure monitoring apparatus which accommodates various fetal positions.

It is also an object of the present invention to provide an apparatus for intrauterine monitoring which can be inserted without the attendant problems associated with the use of a separate, rigid guide tube.

It is a further object of the present invention to provide an apparatus for intrauterine monitoring which minimizes the risk of inaccurate pressure measurements due to interference of intrauterine fluids, tissue, and/or air bubbles entrapped in the system.

Another important object of the present invention is to provide an intrauterine pressure monitoring apparatus wherein one side of the diaphragm of the pressure transducer is continuously vented to atmospheric pressure.

Additionally, it is an object of the present invention to provide an intrauterine pressure monitoring apparatus which can be readily calibrated and does not require rezeroing or balancing when the patient changes position even after the transducer has been inserted inside the uterus.

It is yet another object of the present invention to provide an intrauterine monitoring apparatus which allows fluid samples to be withdrawn from, and fluids to be infused into, the uterus.

It is still another object of the present invention to provide an apparatus for monitoring fetal heart rate which does not require an electrode puncturing, or being attached to, the skin of the fetus.

Still another object of the invention is to provide an apparatus for intrauterine pressure and fetal heart rate monitoring wherein a plurality of alternative signals are generated based on the fetal heart rate, so that an optimal signal can be used.

Additional objects and advantages of the invention will be apparent from the description and claims which follow, or may be learned by the practice of the invention.

Briefly summarized, the foregoing objects and advantages are realized in a novel disposable apparatus for montoring intrauterine pressure and fetal heart rate, wherein the apparatus comprises: a cable means for providing a plurality of electrical conductors and through which a stiffener means is used for purposes of stiffening the cable means when it is to be inserted into the uterus or other body compartment of a patient; a pressure transducer located at the distal end of the cable means for monitoring intrauterine or compartmental pressures, the pressure transducer having a first side in fluid communication with the intrauterine or compartmental pressure, and a second side which is in fluid communication with atmospheric pressure; vent means for introducing through the cable means the atmospheric pressure to the second side of the transducer diaphragm; plug means for coupling the cable means to a monitoring device; and electrode means disposed at the distal end of the cable means for receiving electrical signals generated by the heart of a fetus. The pressure transducer is electrically insulated from the surrounding environment by an insulation layer. In one embodiment, the pressure transducer is surrounded by a flexible boot. The flexible boot reduces the chances of tissue damage occurring during use or insertion of the apparatus.

In one embodiment a stylet is permanently disposed within the cable as the stiffener means. In another embodiment, the stylet is removable which allows a physician to insert the apparatus into the mother's uterus without the aid of a guide tube and, once the apparatus is in position, the stylet may be removed causing the cable to become more flaccid, and also thereby providing a lumen through which amniotic fluid may be sampled or fluids infused into the uterus.

Within the cable are a plurality of electrical conductors or wires. Also provided in the apparatus of the present invention is a vent means which may be comprised of a vent channel or tube in the cable for venting the back side of the pressure transducer diaphragm to the atmosphere. Additionally, means are provided to apply a calibration pressure to the side of the diaphragm that is vented by way of the vent channel.

The heart rate monitoring function of the apparatus is carried out by the electrode means, which preferably comprises one or more electrodes disposed on the exterior surface of the leading end of the cable. Preferably the electrodes comprise metallic bands disposed about the circumference of the cable. Each electrode is electrically connected to one of the conductors in the cable allowing the fetal EKG and heart rate to be detected. Each electrode pair produces a signal corresponding to the fetal heart rate, so that any one of the signals so produced can be utilized depending upon which signal is best.

BRIEF DESCRIPTION OF THE DRAWINGS

In order to more fully understand the manner in which the above-recited objects and advantages of the invention are obtained, a more particular description of the invention will be rendered by reference to specific embodiments thereof which are illustrated in the appended drawings. Understanding that these drawings depict only typical embodiments of the invention and are therefore not to be considered limiting of its scope, the presently preferred embodiments and the presently understood best mode of the invention will be described with additional detail through use of the accompanying drawings in which.

DETAILED DESCRIPTION OF THE PREFERRED EMBODIMENTS

It will be readily appreciated that the components of the present invention, as generally described and illustrated in the figures herein, could be arranged and designed in a wide variety of different configurations. For example, although the first embodiment described herein is particularly useful for measuring intrauterine pressure, the apparatus of the first embodiment may be adapted to a wide number of intracompartmental pressure monitoring applications, including but not limited to, intra-articular, esophageal, intra-intestinal and/or intracranial monitoring. In contrast, the second embodiment described herein is designed to monitor both intrauterine pressure and fetal heart rate.

Figure 1:
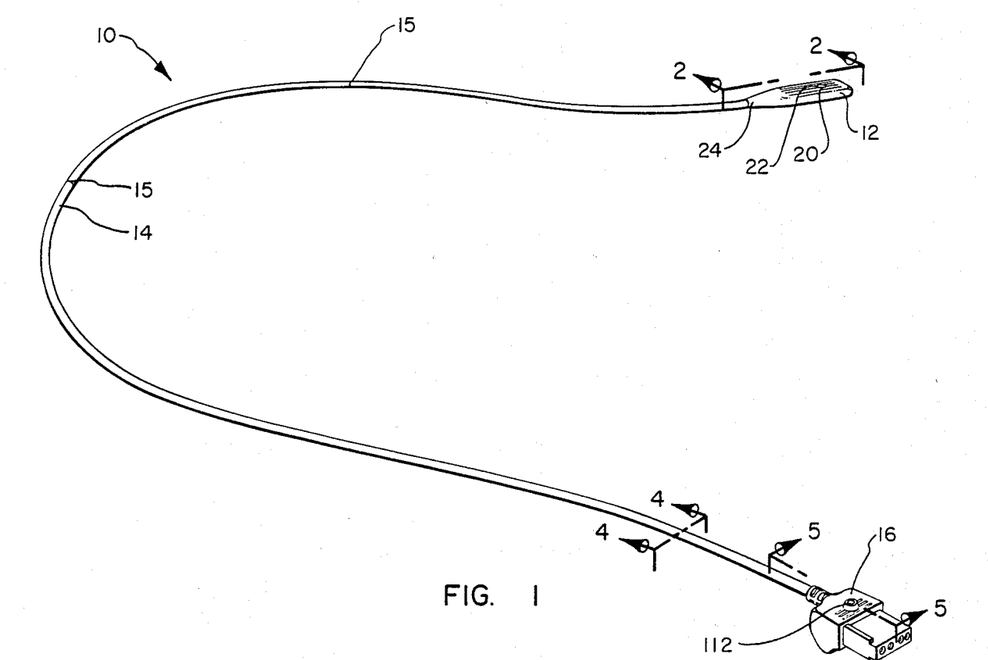
FIG. 1 is a perspective view illustrating a first presently preferred embodiment of the apparatus of the present invention.

Referring first to FIG. 1, the various pressure sensing components of transducer apparatus 10, which will be described in more detail below, are contained within a flexible boot 12. As illustrated, boot 12 is provided with a hole 20 which communicates with the pressure sensing components. In addition, a cable 14 extends from boot 12 and serves to carry electrical signals which represent the pressure measurements made by transducer apparatus 10 to a monitor (not shown).

Figure 6:
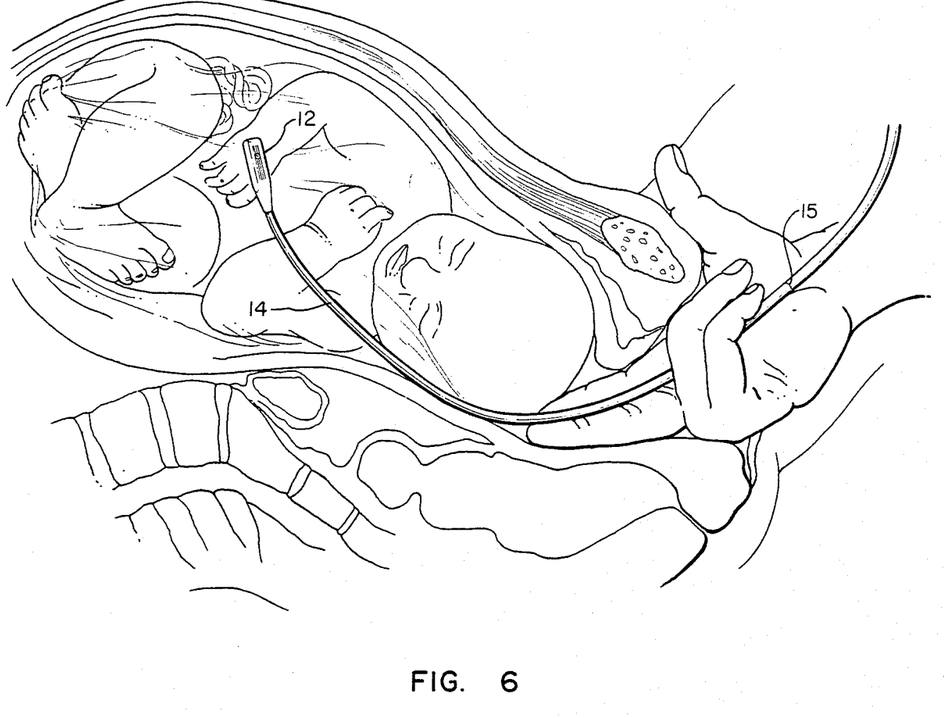
FIG. 6 is a perspective view illustrating placement of the first embodiment within a uterus to measure intrauterine pressure during childbirth.

In use, flexible boot 12 of transducer apparatus 10 is inserted into the uterus or other body compartment of a patient as shown in FIG. 6 and as more fully described hereinafter. The pressure detection components within boot 12 detect and measure the intracompartmental fluid pressure and generate electrical signals representing the pressure. The generated electrical signals are then transmitted along cable 14 to a plug 16, and plug 16 is connected to a monitor (not shown) such that the pressure data may be appropriately displayed and/or recorded.

Figures 2, 3, 4, 5:
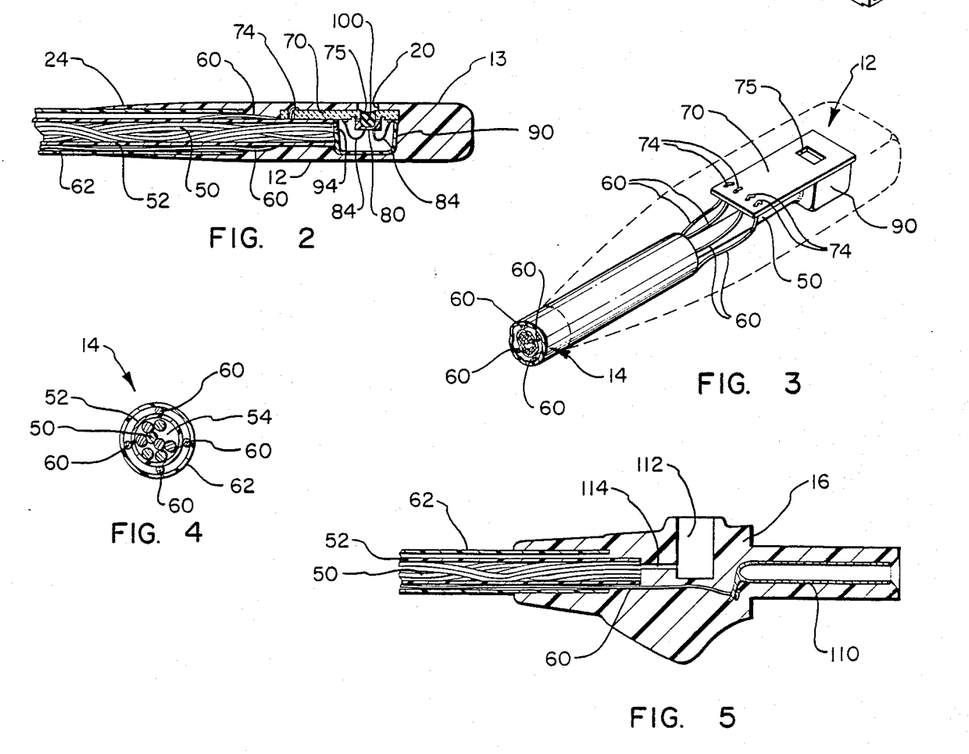
FIG. 2 is a cross-sectional view of the first embodiment taken along line 2—2 of FIG. 1.
FIG. 3 is a perspective view illustrating the configuration of the pressure sensing components within the flexible boot of the first embodiment, the flexible boot being shown by the broken lines.
FIG. 4 is a cross-sectional view of the electrical cable of the first embodiment taken along line 4—4 of FIG. 1.
FIG. 5 is a cross-sectional view of the plug on the electrical cable of the first embodiment taken along line 5—5 of FIG. 1.

One presently preferred embodiment for the pressure sensing components of transducer apparatus 10 is illustrated in FIGS. 2 and 3. As shown, these pressure sensing components comprise a pressure transducer 80 which is mounted on a substrate 70.

Pressure transducer 80 is formed by methods which are well-known in the art so as to include the required piezoresistive pressure diaphragm and measuring circuitry. For example, four resistive elements are ion-implanted on pressure transducer 80 so as to form a conventional Wheatstone bridge. In addition, a central portion of pressure transducer 80 is etched away (such as, for example, by chemical etching techniques), so as to form a piezoresistive diaphragm. If, for example, pressure transducer 80 is 0.020 inches (0.508 mm) thick, the central diaphragm of pressure transducer 80 could be formed so as to be approximately 0.0015 inches (0.0381 mm) thick.

As illustrated in FIGS. 2 and 3, substrate 70 has a hole 75 therethrough. Pressure transducer 80 is mounted to substrate 70 such that the piezoresistive diaphragm of pressure transducer 80 is positioned directly over hole 75 in substrate 70.

Pressure transducer 80 is mounted to substrate 70 such that thermal expansion and contraction of pressure transducer 80 will not subject pressure transducer 80 to mechanical stress which might cause incorrect, transient pressure readings. Thus, for example, pressure transducer 80 is secured with an adhesive material which is flexible enough to permit pressure transducer 80 to thermally expand and contract without significant interference. Such an adhesive may, for example, comprise a suitable silicone adhesive.

As depicted in FIG. 2, the central diaphragm of pressure transducer 80 is electrically connected to other circuitry on substrate 70 that is provided for purposes of temperature compensation as described further below. For example, solder pads may be provided on substrate 70, and the diaphragm of pressure transducer 80 can be electrically connected to the solder pads on substrate 70 by means of wires 84 or flex circuit solder bumps.

Substrate 70 may be formed of any of a number of suitable dielectric materials, such as, for example, a ceramic material. Substrate 70 is preferably provided with a conventional temperature compensation circuit which is used to adjust both the zero pressure point and the gain of transducer apparatus 10 such that these parameters will not change with variations in temperature. Such a temperature compensation circuit also determines the gain or sensitivity of transducer apparatus 10, such gain being typically on the order of approximately five microvolts per volt of excitation per millimeter of mercury pressure. Further, the temperature compensation circuit is used to match the input and output impedance of transducer apparatus 10 with that of the monitor device (not shown), typical impedances being about 350 ohms. This compensation can also be placed on the sensor 80 by using thin film processing.

A temperature compensation circuit may be provided on substrate 70 in any suitable manner. For example, the temperature compensation circuit may be provided using appropriate thick film silk-screening techniques. Thereafter, the various components of the temperature compensation circuit may be laser-trimmed to the required values by means which are known in the art.

Substrate 70 is also provided with a means for electrically connecting the circuitry on substrate 70 and pressure transducer 80 to the conductors 60 of cable 14. For example, substrate 70 may be provided with solder pads at 74, and conductors 60 may be connected to the solder pads at 74 in a conventional manner.

A cap 90 is secured to substrate 70 so as to cover pressure transducer 80. Cap 90 thus protects pressure transducer 80, together with the associated wires 84, from mechanical injury. Cap 90 is secured to substrate 70 by means of a suitable adhesive, such as, for example, a U.V. cure adhesive. The substrate 70, with associated compensation circuitry, with transducer 80 joined and electrically connected thereto, and cap 90 together comprise the basic transducer means for sensing intracompartmental fluid pressures.

The transducer means comprising substrate 70, transducer 80, and cap 90 is housed within a protective flexible boot 12, which serves as a protective cushion means. Boot 12 may have virtually any suitable configuration which will allow for insertion of boot 12 into the uterus or other body compartment for which the apparatus is designed. In order to protect the patient against injury, boot 12 is preferably formed of a soft flexible material, such as, for example, low durometer PVC or silicone (45 Shore A), and boot 12 extends substantially beyond the end of substrate 70 and cap 90 to form a flexible cushion 13 at the leading end of the boot.

To protect the electrical components of transducer apparatus 10 from exposure to moisture within the uterus or other intracompartmental environment, the open end 24 of boot 12 is sealed in some manner to the outer insulation layer 62 of cable 14. Boot 12, may, for example, be vacuum formed or heat bonded around the end of cable 14. Alternatively, boot 12 can be secured to insulation layer 62 of cable 14 using a suitable waterproof adhesive.

Boot 12 is provided with a hole 20 which is positioned so as to be in alignment with hole 75 in substrate 70. As described further below, hole 20 permits pressure pulses to be transmitted through boot 12 so as to be detected by transducer 80. Advantageously, in order to prevent fluids or tissue from obstructing hole 20 and thus interfering with the pressure measurements, boot 12 may be provided with a plurality of grooves 22 surrounding hole 20, as illustrated in FIG. 1.

As shown in FIG. 2, hole 20 in boot 12 and hole 75 in substrate 70 can be filled with a suitable dielectric material 100, such as, for example, a gel material. Gel material 100, which fills the holes 75 and 20 of substrate 70 and boot 12 provides a means for hydraulically coupling the diaphragm of transducer 80 to intracompartmental fluids so that the fluid pressure can thereby be transmitted to transducer 80 and sensed. Gel 100 may comprise a silicone gel. Gel 100 also forms a fluid-tight seal between boot 12 and substrate 70 and electrically isolates substrate 70 and its associated circuitry from the amniotic or other body fluids surrounding the transducer. This increases the safety of the device by helping to minimize any electrical shock hazard to the patient.

The structure and method of manufacturing the presently preferred pressure sensing components of transducer apparatus 10, which are described above, are further set forth in U.S. Pat. No. 4,576,181, issued Mar. 18, 1986 for DISPOSABLE PRESSURE TRANSDUCER APPARATUS FOR MEDICAL USE, which is incorporated herein by reference.

In order to facilitate insertion of boot 12 into the uterus or other body compartment of a patient, cable 14 is preferably provided with a stiffener means which, in the first preferred embodiment, is comprised of stylet 50 (see FIGS. 2 and 3). The use of a stylet 50 in cable 14 obviates the need for using a rigid guide tube of some sort as must be used with conventional intrauterine pressure sensing techniques, so that cable 14 can be used for insertion of the transducer. In addition, the interstices of the stylet form a vent channel 54. Cable 14 can be provided with a stylet 50 in any of a number of different ways. One presently preferred configuration for a cable 14 which includes a suitable stylet 50 is illustrated in FIG. 4.

As shown, cable 14 comprises a stranded steel stylet 50 which is surrounded by an insulating sheath 52. Conductors 60 of cable 14 are positioned on the outside of insulating sheath 52, as shown.

Conductors 60 may be any suitable electrical conductors. For example, conductors 60 may be magnet wire conductors. Advantageously, since magnet wires are typically already insulated, they do not require a separate insulation coating. To provide further insulation and a smooth outer surface to cable 14, an outer insulating sheath 62 is provided. Thus, the overall cable means of the first embodiment is comprised of stylet 50, insulating layer or sheath 52, conductors 60 and outer insulation layer or sheath 62.

In order to obtain accurate pressure measurements, the pressure readings of transducer apparatus 10 should be referenced to some substantially constant pressure. This may easily be done by using a vent means to reference the pressure readings to atmospheric pressure. To this end, the interior of cap 90 surrounding transducer chip 80 is continuously vented to atmospheric pressure by means of a vent channel 54 (see FIG. 4) in cable 14. The vent channel 54 communicates both with the interior of cap 90, through a vent hole 94 (FIG. 2) in cap 90 and with the atmosphere through a suitable vent port 112 (FIGS. 1 and 5) located somewhere along cable 14, such as, for example, in a plug 16 at the end of cable 14. Thus, by providing an air passageway to and from cap 90, the vent channel 54 of cable 14 assures that the side of the transducer diaphragm covered by cap 90 is continuously referenced to atmospheric pressure.

The vent channel 54 may be provided in cable 14 in a number of different ways. Some of the ways for providing a suitable vent channel in cable 14 are set forth in the above-referenced patent. For purposes of the first presently preferred embodiment, it is preferred that the vent channel in cable 14 be provided by means of the stylet 50 in cable 14.

As discussed previously and as illustrated in FIG. 4, stylet 50 may comprise a cable having multiple strands of steel wire. In such case, the vent channel 54 in stylet 50 may be provided by removing one of the steel wires from stylet 50. Stylet 50 may then be bonded to cap 90, as depicted in FIG. 2, so that the vent channel 54 in stylet 50 communicates through vent hole 94 with the interior of cap 90.

The distal end of cable 14 is provided with a suitable connector, such as, for example, a plug 16. Plug 16 may be formed of any suitable material, for example, a plastic material prepared by means of injection molding or by other means which are well-known in the art. Plug 16 may then be bonded by means of an adhesive or by means of heat-bonding to the external insulative sheath 62 of cable 14.

As depicted in FIG. 5, the conductors 60 of cable 14 are electrically connected to contacts 110 within plug 16. Contacts 110 may then be coupled to appropriate leads such that conductors 60 can be properly connected to a monitor/display device.

A hole 112 is formed in plug 116 and communicates with a bore 114, as shown in FIG. 5. Bore 114 communicates with vent channel 54 (see FIG. 4) of stylet 50. Thus, since space 54 communicates with the interior of cap 90, as described above and illustrated in FIG. 2, the interior of cap 90 is continuously vented to atmospheric pressure through space 54 and stylet 50, together with bore 114 and hole 112 in plug 16.

Advantageously, hole 112 can also be used to calibrate the pressure monitoring system. For example, a vacuum can be imposed through hole 112, bore 114, and vent channel 54 in stylet 50 on the backside of transducer 80 within cap 90. Since transducer 80 is a true differential device, a vacuum on the backside of the diaphragm of transducer 80 is completely equivalent to a pressure on the patient's side of the transducer. The method for calibrating the pressure monitoring system using hole 112 in plug 16 is disclosed more fully in U.S. Pat. No. 4,610,256, issued Sept. 9, 1986 for PRESSURE TRANSDUCER, which is incorporated herein by reference.

The manner in which transducer apparatus 10 may be used is illustrated, for example, in FIG. 6, which shows an intrauterine application. The patient should be in the dorsal lithotomy position, the uterine membrane ruptured, and the cervix adequately dilated. Using the hand and fingers as shown to guide the apparatus, it is inserted into the cervix until it is well into the amniotic space for intrauterine monitoring. Insertion should be performed carefully and gently, without force. Any cervical quadrant may be used. Stylet 50 of cable 14 must have a desired rigidity so that for intrauterine monitoring, the apparatus will accommodate insertion of the boot 12 past the fetal head while manipulating the apparatus from outside the introitus. Importantly, since the transducer is inside the patient at the catheter tip, zeroing is not a problem, and attendant inaccuracies in this regard are eliminated since the transducer is positioned at the desired reference level.

If desired, markings 15 (see FIG. 1) may be placed on cable 14 at suitable intervals (for example, one mark at 12 inches and two marks at 18 inches), to assist the physician or nurse in determining depth of insertion. Total length of the apparatus is approximately 3 feet (80 cm), with the flexible boot containing the transducer being about 0.35" (0.77 cm) × 0.2" (0.44 cm) × 0.61" (1.34 cm). The cable 14 with stylet 50 is preferably about 0.160" (0.41 cm) wide.

Since cable 14 of transducer apparatus 10 includes a stiffening stylet 50, transducer apparatus 10 can be inserted into the uterus without the use of a rigid guide tube as required with conventional intrauterine pressure monitoring techniques. Further, since the present invention does not require the use of a fluid-filled catheter inserted into the uterus, the present invention does not suffer from the disadvantages associated with amniotic fluid or air bubbles entering the catheter, or the problem of continuously balancing the zero of the transducer.

Boot 12 of transducer apparatus 10 is also designed so as to increase safety by providing a soft cushion at the tip of the catheter, as well as preventing obstruction by intrauterine tissue. Specifically, grooves 22 on the surface of boot 12 prevent intrauterine tissue from sealing hole 20 and interfering with accurate pressure measurements.

The semiconductor transducer 80 of transducer apparatus 10 is continuously vented to atmosphere through a vent channel formed in stylet 50 which extends along the length of cable 14 of transducer apparatus 10 to a hole in plug 16 on cable 14. Advantageously, the vent channel can also be used to calibrate the semiconductor transducer directly using a known pressure source, even when the transducer is inside the uterus or other body compartment.

A second embodiment of the present invention is illustrated in FIGS. 7-11. Once again, like parts are designated with like numerals throughout.

This embodiment is particularly adapted for monitoring fetal heart rate as well as the intrauterine pressure. As illustrated best in FIG. 7, the apparatus generally comprises a cable 208 having a flexible outer insulative sheath or covering. Provided within the leading end of the apparatus, generally indicated at 200, is a pressure transducer. The structure through which the intrauterine pressure pulses are communicated to the pressure transducer is indicated at 202 in FIG. 7. Also illustrated near the leading end of cable 208 is lumen orifice 204. These structures will be explained more fully in connection with FIG. 8.

In some cases, a physician desires to sample amniotic fluid withdrawn from the uterus or to infuse fluids into the uterus. In order to accomplish these functions, disposed within cable 208 is lumen tube 236, shown protruding from plug 210 in FIG. 7, which opens into lumen orifice 208 as will be explained in more detail below. Also, lumen tube 236 is provided with male luer connector 218, which is engaged by a female luer connector 220 which serves as a plug for sealing the end of lumen tube 236.

In order to eliminate the need for using a guide tube to insert the apparatus into the uterus, a stiffening means is disposed within cable 208. In contrast to the permanent stylet described in connection with the first embodiment, the embodiment illustrated in FIGS. 7-11 incorporates a removable stylet as a stiffening means. The removable stylet comprises a slender metal rod 238 which is inserted into lumen tube 236.

Figure 11:
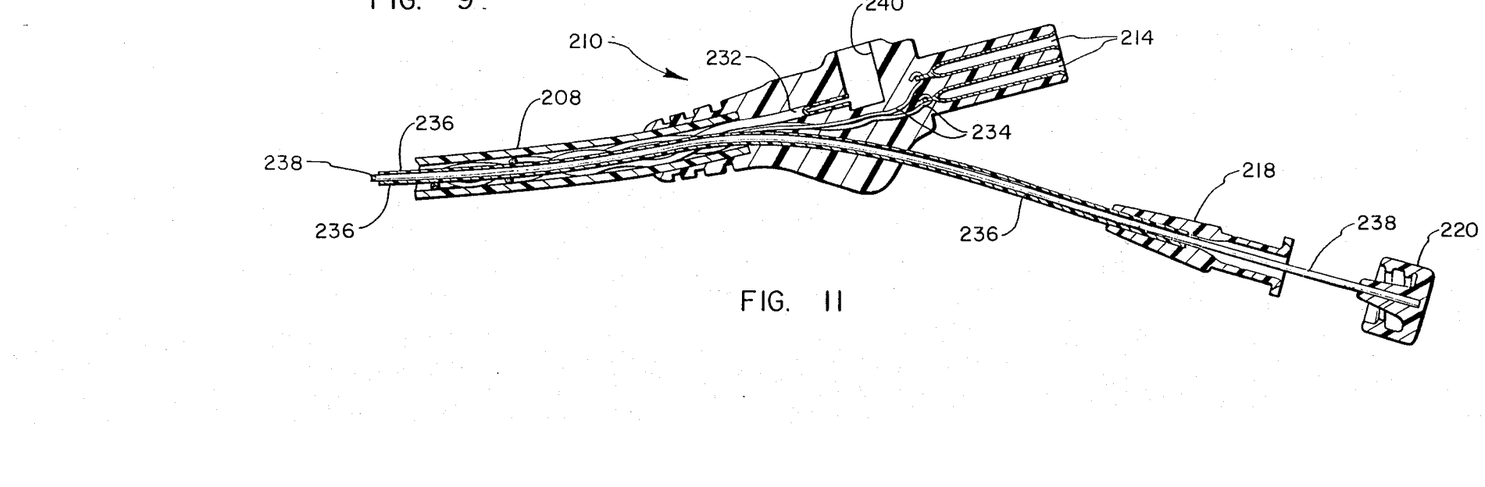
FIG. 11 is a cross-sectional view of the second embodiment taken along line 11—11 of FIG. 7.

As shown best in FIG. 11, the removable stylet 238 may be permanently attached to plug 220, which also serves as a handle to use during the insertion or withdrawal of stylet 238. Advantageously, once the apparatus is inserted into the uterus, the removable stylet 238 may be withdrawn and the cable means becomes flaccid. Thus, any risk of tissue damage due to tearing or puncturing by the leading end of the apparatus is reduced. Furthermore, tube 236 may also then serve as a conduit through which samples of amniotic fluid may be withdrawn, or through which medication may be introduced into the uterus, by means of luer connector 220.

Figure 7:
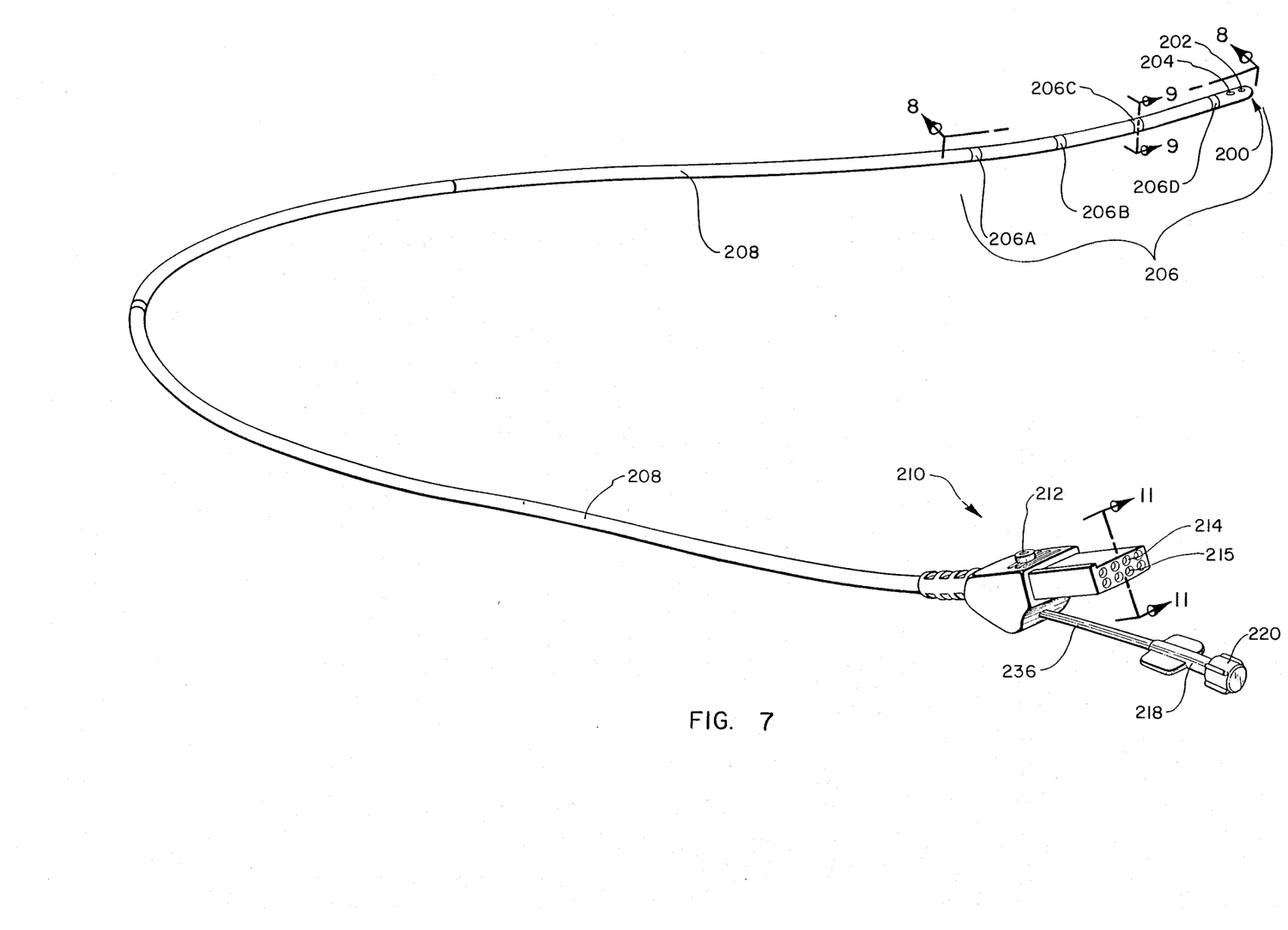
FIG. 7 is a perspective view illustrating a second presently preferred embodiment of the apparatus of the present invention which includes structures used to monitor the fetal heart rate.

The apparatus illustrated in FIG. 7 is provided with a semiconductor pressure transducer which is small enough to fit within the diameter of cable 208. Preferably, the outer diameter of cable 208 is approximately 0.15 inches or less. As in the case of the other embodiment, the entire transducer assembly is enclosed within a soft covering which serves as a boot for enclosing the transducer assembly and for cushioning the end of the apparatus. As shown best in FIG. 8, the end of the cushioning boot 201 is brought to a gently sloping, rounded point to facilitate insertion, and the overall diameter of the entire apparatus is essentially uniform throughout its length.

Similar to the previously described embodiment, the apparatus of FIG. 7 is provided with a vent channel within cable 208 extending from the back side of the pressure transducer diaphragm to vent hole 212 in plug 210. Vent hole 212 is normally left open to the atmosphere and may be used for calibrating procedures as described earlier.

In order to monitor the heart rate of the fetus, electrode means are provided on the external circumference of cable 208. In the preferred embodiment, the electrode means comprise a plurality of electrodes 206A-D individually electrically connected to one of sockets 214 provided in plug 210. Likewise, each of the four electrical conductors connected to the pressure transducer as previously described in connection with the first embodiment is also individually connected to one of the sockets 215 in plug 210.

Figure 8:
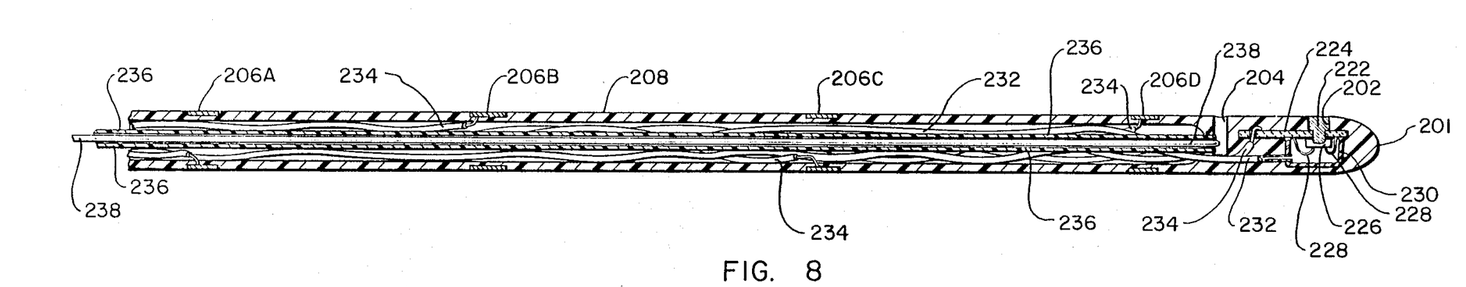
FIG. 8 is a cross-sectional view of the second embodiment taken along line 8—8 of FIG. 7.

The internal construction of the second embodiment can be best appreciated by an examination of FIGS. 8-11. FIG. 8 is a cross-sectional view of the leading end of the embodiment taken along line 8—8 of FIG. 7. Similar to the structure of the pressure transducer of the first embodiment, the second embodiment, as shown best in FIG. 8, includes a pressure transducer substrate 224 upon which is mounted transducer diaphragm 226 which is enclosed on one side by cap 230.

The construction of the pressure transducer of the second embodiment may be identical or similar to the construction of the pressure transducer described in connection with the first embodiment with the understanding that the uniform outer diameter of cable 208 requires that the pressure transducer be smaller than the cable diameter.

Pressure transducer diaphragm 226 is electrically connected to the electrical conductors formed on substrate 224 in the same fashion described in connection with the first embodiment by way of wires 228. As in the first embodiment, the signals from the pressure transducer are conveyed to plug 210 (shown in cross-section in FIG. 11) by way of individual wires, one of which is represented at 234 in FIG. 8.

As illustrated in FIG. 8, the pressure transducer is embedded within the leading end of cable 208 and a hole 202 is provided through the outer surface of cable 208 so that the intrauterine pressure may be communicated to the transducer diaphragm 226. It will be appreciated that it is desirable to provide some means for insulating the pressure transducer from the surrounding intrauterine environment while still permitting fluid communication with the intrauterine pressure pulses. Thus, hole 202 is filled with a dielectric gel material as previously described in connection with the first embodiment. Dielectric gel material 222 serves to both electrically insulate the pressure transducer, in cooperation with the leading end of the cable, as well as serving to transmit the intrauterine pressure pulses to the transducer diaphragm 226.

Also illustrated in FIG. 8 is vent tube 232 which is in communication with the interior of cap 230. As explained earlier, it is preferred that the back side of pressure diaphragm 226 which is contained within cap 230 be vented to atmospheric pressure during use. Also, vent tube 232 may be used to apply a known pressure to the pressure transducer for calibration purposes.

Figures 9, 10:
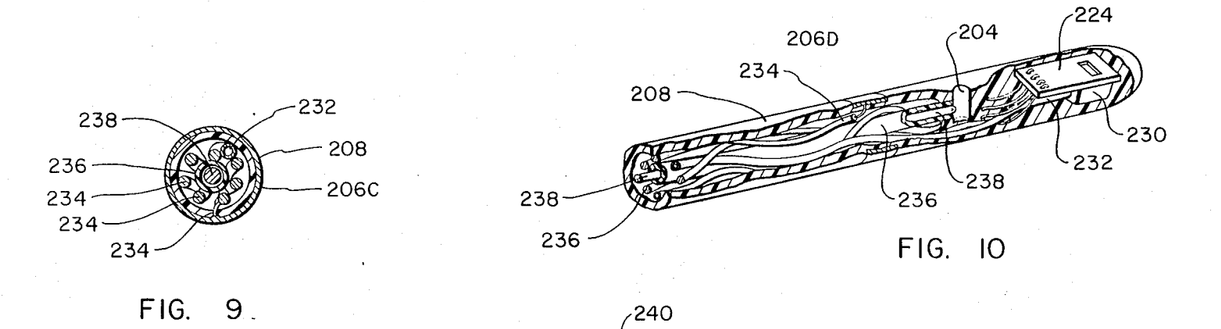
FIG. 9 is a cross-sectional view of the second embodiment taken along line 9—9 of FIG. 7.
FIG. 10 is a partially cut away perspective view of the leading end of the second embodiment.

An overall view of the structure of the pressure transducer can be seen in the partially cut away perspective view of FIG. 10. In the view provided in FIG. 10, substrate 224, cap 230, and vent tube 232 may be readily observed.

As mentioned, the second embodiment is provided with a lumen tube 236 through which amniotic fluid may be sampled or fluids infused into the uterus. As shown in FIGS. 8 and 10, lumen orifice 204 is in communication with lumen tube 236.

Lumen tube 236 performs two functions in the second embodiment. In addition to allowing the sampling of amniotic fluid and the infusion of fluids into the uterus, lumen tube 236 serves as a guide for removable stylet 238. Stylet 238 can be seen in its fully inserted position in FIGS. 8 and 10. Lumen tube 236 extends out of the distal end of cable 208 through plug 210 as shown best in FIG. 11. Thus, lumen tube 238 may be readily connected to additional tubing which may lead to an infusion pump, syringe or other medical device.

As mentioned, the second embodiment of the present invention is provided with a plurality of electrodes 206A-D disposed about the circumference of the cable. Electrodes 206A-D are preferably comprised of highly conductive material such as a chromium tape which forms a band around the outer sheath of cable 208.

It is presently preferred that electrodes 206A-D are equally spaced along cable 208 at a distance of about one inch to about four inches apart. It will be appreciated that it is within the scope of the present invention to vary the electrode spacing as well as to utilize only one, or more than four, electrodes along the cable.

Importantly, the purpose of including a plurality of electrodes is to provide a plurality of signals from which to determine the fetal heart rate. For example, the best signal (i.e., the signal with the greatest signal-to-noise ratio) may be obtained by use of electrode pair 206A and 206D. Alternately, use of another pair of electrodes or a single electrode with a common maternal electrode may provide the best fetal heart signal.

Since the exact placement of the electrodes within the uterus in relation to the fetus is difficult to determine after insertion of the apparatus, it is also advantageous to provide a plurality of electrodes in order to obtain several signals from which the best possible fetal heart rate signal may be selected. It will be appreciated that once in place, both fetal EKG as well as the fetal heart rate may be readily recorded or observed using appropriate monitoring devices. Such monitoring devices will desirably include circuitry to multiplex the plurality of signals received from the second apparatus to derive therefrom the optimal fetal signal.

The structure of the electrodes as well as the internal structure of the apparatus can be additionally understood by reference to FIG. 9. FIG. 9 is a cross-sectional view through the circumference of electrode 206C and cable 208. Thus, in FIG. 9, electrode 206C is shown surrounding the outer sheath of cable 208. Electrode 206C is directly connected to one of individual conductors 234. The conductors 234 may be connected to the electrodes in one of the many ways known to those skilled in the art. Also illustrated in FIG. 9 is vent tube 236 as well as removable stylet 238 and lumen tube 236.

It will be appreciated that the interior of cable 208 must be kept sealed from its surrounding environment. Thus, all the connections with the electrodes as well as the junction between lumen tube 236 and lumen orifice 204 (FIG. 10) must be fluid tight. Additionally, it will be realized that ease of insertion into the uterus is an important consideration when fabricating an embodiment of the present invention. Thus, as mentioned, the outer circumference of cable 208 should be smooth and free of any potentially damaging protrusions.

In order to reduce friction between cable 208 and the surrounding body tissue, a hydrogel material may preferably be applied to at least a portion of the outer surface of cable 208. One particular hydrogel material which may be used with the present invention is marketed under the HYDROMER ® trademark by Hydromer, Inc. of Whitehouse, New Jersey.

The hydrogel materials suitable for use with the present invention share the characteristic of retaining water and swelling when they are wetted thus reducing the coefficient of friction between the coating and surrounding tissue.

Illustrated in FIG. 11 is a cross-sectional view of plug 210 and the distal end of cable 208. Plug 210 should preferably be in fluid tight engagement with cable 208 using techniques described previously in connection with the first embodiment. As can be seen in FIG. 11, lumen tube 236 extends through plug 210 and terminates in luer lock connector 218. Luer lock connector 218 has been fashioned to ease insertion and removal of stylet 238 as well as easily attach to additional medical tubing.

Stylet 238 is shown partially removed from lumen tube 236. Removable stylet 238 is preferably a smooth slender rod of flexible stainless steel with a rounded leading end. As shown in FIG. 8, it is preferred that removable stylet 238, when fully inserted into lumen tube 236, reach to lumen orifice 204. Plug 220 is provided on the end of stylet 238 to both facilitate removal of stylet 238 and to provide a fluid tight plug for connector 218.

In a fashion similar to that described in connection with FIG. 1, vent hole 240 in plug 210 is in communication with vent tube 232. Thus, the back side of the pressure transducer diaphragm may be vented to the atmosphere or a calibration pressure may be applied thereto. Also, conductors 234 are individually connected to plug sockets 214.

The invention may be embodied in other specific forms without departing from its spirit or essential characteristics. The described embodiments are to be considered in all respects only as illustrative and not restrictive. The scope of the invention is, therefore, indicated by the appended claims, rather than by the foregoing description. All changes which come within the meaning and range of equivalency of the claims are to be embraced within their scope.

What is claimed and desired to be secured by United States Letters Patent is:

1. An apparatus for monitoring intrauterine pressure pulses and fetal heart rate, comprising:
   a pressure transducer having a diaphragm with first and second sides, said first side being in communication with said intrauterine pressure pulses;
   cable means for providing a plurality of electrical conductors, at least two of said plurality of conductors being connected to said pressure transducer;
   vent means for introducing atmospheric pressure to said second side of said diaphragm;
   means for connecting the plurality of electrical conductors to a monitoring device; and
   a pair of electrode means for independently receiving electrical signals through amniotic fluid generated by the heart of a fetus, each said electrode means being located on an outside surface of said cable means so as to be in electrical contact with said amniotic fluid and being positioned at a leading end of said cable means adjacent said transducer such that when said leading end is inserted into the uterus of a patient, each said electrode means senses fetal heart rate through amniotic fluid within the uterus, each said electrode means being connected to at least one of the plurality of electrical conductors such that the fetal heart rate and the intrauterine pressure may be displayed by said monitoring device.

2. An apparatus for monitoring intrauterine pressure pulses and fetal heart rate as defined in claim 1 wherein each said electrode means comprises an electrode disposed on said cable means.

3. An apparatus for monitoring intrauterine pressure pulses and fetal heart rate as defined in claim 2 wherein said electrode means further comprises a third electrode and a fourth electrode disposed on said cable means and said third and fourth electrodes are each individually connected to at least one of said plurality of electrical conductors.

4. An apparatus for monitoring intrauterine pressure pulses and fetal heart rate as defined in claim 2 or claim 3 wherein said electrodes comprise metallic bands disposed about the circumference of said cable means.

5. An apparatus for monitoring intrauterine pressure pulses and fetal heart rate as defined in claim 2 or claim 3 wherein said electrodes are spaced a distance apart on said cable means.

6. An apparatus for monitoring intrauterine pressure pulses and fetal heart rate as defined in claim 1 wherein said pressure transducer is positioned near the leading end of the cable means and said pressure transducer fits within the diameter of said cable means.

7. An apparatus for monitoring intrauterine pressure pulses and fetal heart rate as defined in claim 1 further comprising a hydrogel coating applied to the circumference of said cable means at said leading end thereof, the hydrogel coating adapted to decrease the coefficient of friction of said cable means.

8. An apparatus for monitoring intrauterine pressure pulses and fetal heart rate as defined in claim 1 wherein said pressure transducer comprises substrate means onto which said diaphragm is mounted, and cap means joined to said substrate means so as to form a protective cover over said diaphragm.

9. An apparatus for monitoring intrauterine pressure pulses and fetal heart rate as defined in claim 1 wherein the leading end of said cable means is rounded so as to avoid tissue damage and is sufficiently small so as to be easily inserted past a fetus in the cervical region.

10. An apparatus for monitoring intrauterine pressure pulses and fetal heart rate as defined in claim 1 further comprising a cushioned boot disposed about the pressure transducer.

11. An apparatus for monitoring intrauterine pressure pulses and fetal heart rate as defined in claim 10 further comprising means for communicating the pressure pulses through the cushioned boot to the first side of the diaphragm.

12. An apparatus for monitoring intrauterine pressure pulses and fetal heart rate as defined in claim 11 wherein said communication means comprises a dielectric material and openings formed through said substrate means and said cushioned boot, said openings receiving and holding said dielectric material adjacent to said first side of said diaphragm.

13. An apparatus for monitoring intrauterine pressure pulses and fetal heart rate as defined in claim 1 wherein said means for connecting the plurality of electrical conductors comprises a plug connected to the cable means, the plug having a channel formed therein, said channel being in communication with said vent means.

14. An apparatus for monitoring intrauterine pressure pulses and fetal heart rate as defined in claim 1 further comprising a stiffener means associated with said cable means for stiffening said cable means to accommodate insertion within a body compartment of a patient.

15. An apparatus for monitoring intrauterine pressure pulses and fetal heart rate as defined in claim 14 wherein said cable means comprises means for removably receiving said stiffener means so that said stiffener means may be withdrawn and removed from said cable means after insertion is accomplished.

16. An apparatus for monitoring intrauterine pressure pulses and fetal heart rate as defined in claim 15 wherein said cable means further comprises means for guiding said stiffener means through said cable means as said stiffener means is inserted into and removed from the cable means.

17. An apparatus for monitoring intrauterine pressure pulses and fetal heart rate as defined in claim 16 wherein the means for guiding said stiffener means comprises a lumen disposed within said cable means, said lumen having a first opening near the leading end of the cable means.

18. An apparatus for monitoring intrauterine pressure pulses and fetal heart rate as defined in claim 15 wherein said stiffener means comprises a stylet.

19. An apparatus for monitoring intrauterine pressure pulses and fetal heart rate as defined in claim 1 further comprising a lumen disposed in said cable means, said lumen having a first opening near the leading end of said cable means.

20. An apparatus for monitoring intrauterine pressure pulses and fetal heart rate as defined in claim 1 wherein the vent means comprises a vent tube leading from said second side of said diaphragm to said means for connecting the plurality of electrical connectors, said vent tube opening to the atmosphere.

21. An apparatus for monitoring intrauterine pressure pulses and fetal heart rate as defined in claim 1 further comprising a dielectric gel material disposed over said first side of said diaphragm, said dielectric gel material being adapted for communicating the intrauterine pressure pulses to said diaphragm.

22. An apparatus for monitoring intrauterine pressure pulses and fetal heart rate, comprising:
   a pressure transducer having a diaphragm with first and second sides;
   means for communicating said intrauterine pressure pulses to the first side of said diaphragm;
   means for venting the second side of said diaphragm to atmospheric pressure;
   cable means for providing a plurality of individual conductors, at least two of the individual conductors being connected to said pressure transducer;
   means for connecting the individual conductors to monitoring equipment; and
   a first pair of electrodes spaced one from the other and disposed on said cable means on an exterior surface at a leading end thereof, said first pair of electrodes being adapted for receiving independent of one another electrical signals through amniotic fluid generated by the heart of a fetus when inserted into the uterus of a patient, each of said electrodes being individually connected to at least one of said plurality of individual conductors such that the fetal heart rate may be displayed by said monitoring equipment simultaneously with the intrauterine pressure pulses.

23. An apparatus for monitoring intrauterine pressure pulses and fetal heart rate as defined in claim 22 wherein said electrode means further comprises a second pair of electrodes disposed on the cable means and wherein said second pair of electrodes are each individually connected to at least one of said plurality of electrical conductors.

24. An apparatus for monitoring intrauterine pressure pulses and fetal heart rate as defined in claim 22 or claim 23 wherein said electrodes comprise metallic bands disposed about the circumference of said cable means.

25. An apparatus for monitoring intrauterine pressure pulses and fetal heart rate as defined in claim 23 wherein said first and second pair of electrodes are spaced a distance apart on said cable means.

26. An apparatus for monitoring intrauterine pressure pulses and fetal heart rate as defined in claim 22 wherein said pressure transducer fits within the diameter of said cable means.

27. An apparatus for monitoring intrauterine pressure pulses and fetal heart rate as defined in claim 22 further comprising a hydrogel coating applied to the circumference of said cable means at the leading end thereof, the hydrogel coating being adapted to decrease the coefficient of friction of said cable means.

28. An apparatus for monitoring intrauterine pressure pulses and fetal heart rate as defined in claim 22 wherein said pressure transducer comprises substrate means onto which said diaphragm is counted and cap means joined to said substrate means so as to form a protective cover over said diaphragm.

29. An apparatus for monitoring intrauterine pressure pulses and fetal heart rate as defined in claim 22 wherein the leading end of said cable means is rounded and small so as to avoid uterine wall perforation, irritation or placental abruption.

30. An apparatus for monitoring intrauterine pressure pulses and fetal heart rate as defined in claim 22 further comprising a cushioned boot disposed about the pressure transducer.

31. An apparatus for monitoring intrauterine pressure pulses and fetal heart rate as defined in claim 30 further comprising means for communicating the pressure pulses through the cushioned boot to the first side of the diaphragm.

32. An apparatus for monitoring intrauterine pressure pulses and fetal heart rate as defined in claim 31 wherein said communication means comprises a dielectric material and openings formed through said substrate means and said cushioned boot, said opening being adapted for receiving and holding said dielectric material adjacent to said first side of said diaphragm.

33. An apparatus for monitoring intrauterine pressure pulses and fetal heart rate as defined in claim 22 wherein said means for connecting the plurality of electrical conductors comprises a plug connected to the cable means, the plug having a channel formed therethrough in communication with said means for venting.

34. An apparatus for monitoring intrauterine pressure pulses and fetal heart rate as defined in claim 22 further comprising a stiffener means associated with said cable means for stiffening said cable means to accommodate insertion within a body compartment of a patient.

35. An apparatus for monitoring intrauterine pressure pulses and fetal heart rate as defined in claim 34 wherein said cable means comprises means for removably receiving said stiffener means so that said stiffener means may be withdrawn and removed from said cable means after insertion is accomplished.

36. An apparatus for monitoring intrauterine pressure pulses and fetal heart rate as defined in claim 35 wherein said cable means further comprises means for guiding said stiffener means through said cable means as said stiffener means is inserted into and removed from said cable means.

37. An apparatus for monitoring intrauterine pressure pulses and fetal heart rate as defined in claim 36 wherein the means for guiding said stiffener means comprises a lumen disposed within said cable means, said lumen having a first opening near the leading end of the cable means.

38. An apparatus for monitoring intrauterine pressure pulses and fetal heart rate as defined in claim 35 wherein said stiffener means comprises a stylet.

39. An apparatus for monitoring intrauterine pressure pulses and fetal heart rate as defined in claim 22 further comprising a lumen disposed in said cable means, said lumen having an opening disposed at a position along the length of said cable means.

40. An apparatus for monitoring intrauterine pressure pulses and fetal heart rate as defined in claim 22 wherein the means for venting comprises a vent tube leading from said second side of said diaphragm to said means for connecting the plurality of electrical connectors, said vent tube opening to the atmosphere.

41. An apparatus for monitoring intrauterine pressure pulses and fetal heart rate as defined in claim 22 wherein the means for communicating comprises a dielectric gel material disposed over said first side of said diaphragm, said dielectric gel material being adapted for communicating the intrauterine pressure pulses to said diaphragm.

42. A disposable apparatus for monitoring intrauterine pressure pulses and fetal heart rate, comprising:
  a dielectric substrate, said substrate having a hole formed therethrough;
  a semiconductor pressure transducer having a pressure diaphragm with first and second sides, the pressure transducer being mounted on said substrate such that the first side of the pressure diaphragm is positioned over said hole in the substrate;
  a dielectric material positioned over said diaphragm, said dielectric material communicating the pressure pulses to the first side of the pressure diaphragm;
  a cable having a sheath covering a plurality of wires, at least two of the wires being electrically connected to the pressure transducer, said cable comprising a vent channel formed therethrough;
  a plug connected to the cable, the plug having a channel formed therethrough in communication with the vent channel, said channel of the plug terminating at one end in a hole formed in a side of the plug;
  a lumen disposed within said cable, said lumen having an opening toward the leading end of the cable and having an outlet adjacent the distal end of the cable;
  a removable stylet adapted to be inserted into and withdrawn from said lumen so as to stiffen said cable when inserted therein; and
  at least three electrodes spaced one from the other along the length of said cable and disposed on the exterior surface of the sheath near the leading end thereof, each of the electrodes receiving independent of one another the electrical signal generated through the amniotic fluid by the heart of a fetus.

43. An appaaratus for monitoring intrauterine pressure pulses and fetal heart rate as defined in claim 42 wherein said electrodes comprise metallic bands disposed about the circumference of said cable.

44. An apparatus for monitoring intrauterine pressure pulses and fetal heart rate as defined in claim 42 wherein said pressure transducer fits within the diameter of said cable.

* * * * *

Disclaimer 4,873,986—*William D. Wallace*, Salt Lake City, Utah. DISPOSABLE APPARATUS FOR MONITORING INTRAUTERINE PRESSURE AND FETAL HEART RATE, Patent dated Oct. 17, 1989. Disclaimer filed Oct. 28, 1991, by the assignee, Utah Medical Products.

Hereby enters this disclaimer to claims 1, 2, 4-6, 9, 13, 14, 20-22, 24, 26, 28, 29, 33, 34, and 39-41 of said patent has been disclaimed.

*[Official Gazette December 17, 1991]*

UNITED STATES PATENT AND TRADEMARK OFFICE
CERTIFICATE OF CORRECTION

PATENT NO. : 4,873,986

DATED : October 17, 1989

INVENTOR(S) : WILLIAM DEAN WALLACE

It is certified that error appears in the above-identified patent and that said Letters Patent is hereby corrected as shown below:

Column 3, line 18, "also" should be --Also--
Column 4, line 57, "montoring" should be --monitoring--
Column 18, line 60, "appaaratus" should be --apparatus--

Signed and Sealed this

Seventh Day of January, 1992

Attest:

HARRY F. MANBECK, JR.

*Attesting Officer*     *Commissioner of Patents and Trademarks*